United States Patent [19]

Rodak

[11] Patent Number: 5,470,006
[45] Date of Patent: Nov. 28, 1995

[54] SURGICAL FASTENING APPARATUS WITH LOCKING MECHANISM

[75] Inventor: Daniel P. Rodak, Milford, Conn.

[73] Assignee: United States Surgical Corporation, Norwalk, Conn.

[21] Appl. No.: 928,700

[22] Filed: Aug. 11, 1992

Related U.S. Application Data

[63] Continuation of Ser. No. 704,050, May 22, 1991, abandoned, which is a continuation-in-part of Ser. No. 622,856, Dec. 6, 1990, abandoned.

[51] Int. Cl.⁶ ..................................................... A61B 17/02
[52] U.S. Cl. ................................. 227/176; 227/19; 227/8; 227/178
[58] Field of Search .................................. 227/19, 8, 175, 227/176, 178, 180, 182

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green . |

(List continued on next page.)

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 2070499 | 9/1981 | United Kingdom . |
| 8302247 | 7/1983 | WIPO . |

OTHER PUBLICATIONS

"Disposable EEA Surgical Stapler and Curved Disposable EEA Surgical Stapler", Information Booklet, printed Jan. 1985.
Anderson et al., Surgical Stapling, "Thoraci, Vascular and Esophageal Procedures", pp. 1–101, 1988.
Brolin et al., Surgical Stapling, "Bariatric Procedures for Morbid Obesity", pp. 1–115, 1989.
Flickinger et al., Surgical Stapling, "Gastric and Small Bowel Procedures", pp. 1–145, 1988.
"Auto Suture® Premium Poly CS™–57 Disposable Surgical Stapler," printed 1986, reprinted 1990.
"Auto Suture® Poly CS™–57 Disposable Surgical Stapler", printed Jul. 1988.
"Auto Suture® Poly CS™–57 Disposable Loading Units with Lactomer® Absorbable Copolymer Staples", printed Jul. 1988.

*Primary Examiner*—Rinaldi I. Rada

[57] ABSTRACT

An improved apparatus for applying surgical fasteners to body tissue includes a cartridge containing a plurality of fasteners, an anvil positioned opposite the cartridge, and a locking mechanism to prevent re-approximation of the cartridge towards the anvil after the fasteners are fired and the cartridge is withdrawn from the anvil.

28 Claims, 11 Drawing Sheets

U.S. PATENT DOCUMENTS

| | | |
|---|---|---|
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. . |
| 4,530,453 | 7/1985 | Green . |
| 4,540,110 | 9/1985 | Bent . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | DiGiovanni . |
| 4,592,498 | 6/1986 | Braun et al. . |
| 4,597,517 | 7/1986 | Wagdy . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |
| 4,869,415 | 9/1989 | Fox . |
| 4,881,544 | 11/1989 | Green et al. . |
| 4,881,545 | 11/1989 | Isaacs et al. . |
| 4,892,244 | 1/1990 | Fox et al. . |
| 4,915,100 | 4/1990 | Green . |
| 4,938,408 | 7/1990 | Bedi et al. . |
| 4,941,623 | 7/1990 | Pruitt . |
| 4,955,959 | 9/1990 | Tompkins et al. . |
| 5,031,814 | 7/1991 | Tompkins et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins . |
| 5,129,570 | 7/1992 | Schulze et al. . |

SURGICAL FASTENING APPARATUS WITH LOCKING MECHANISM

CROSS REFERENCE TO RELATED APPLICATIONS

This is a continuation of application Ser. No. 07/704,050 filed on May 22, 1992, which is a continuation-in-part of Ser. No. 07/622,856 filed on Dec. 6, 1990, both abandoned.

BACKGROUND OF THE INVENTION

1. Field of the Invention

This invention relates to surgical fastening apparatus, and specifically to an improved surgical fastening apparatus containing a locking mechanism.

2. Background of the Art

Surgical fastening apparatus for simultaneously applying an array of surgical staples or other types of fasteners are known in the art. Such apparatus are used for suturing body tissue such as, for example, intestinal and gastric walls with spaced parallel rows of longitudinally aligned staples. These surgical stapling apparatus reduce the time of wound closure in a surgical procedure.

Typically these devices include a fastener holder disposed on one side of the tissue to be fastened, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. Optionally, the fastening apparatus may include a knife mechanism for creating an incision between rows of fasteners. The fasteners can be made of metal, non-absorbable polymers, or bioabsorbable polymers such as polyglycolide, polylactide, and copolymers thereof.

In common use are apparatus in which the fastener holder comprises a disposable cartridge removably mounted in or on a permanent actuator for supporting and actuating the cartridge. The cartridge is disposable after a single use, i.e. after the fasteners are fired. The permanent actuator is reusable in the same surgical procedure after reloading with a fresh cartridge, and is reusable in another surgical procedure after cleaning, sterilizing, and reloading. Also known are disposable surgical apparatus, in which the entire apparatus is disposed of after use. Examples of surgical stapling apparatus may be found in U.S. Pat. No. 4,354,628 to Green, U.S. Pat. No. 4,665,916 to Green, and U.S. Pat. No. Des. 283,733 to Rawson et al.

In the use of surgical fasteners the possibility arises that the fastener apparatus may be actuated when the cartridge is empty of fasteners. This can occur when the apparatus has been fired once, but the cartridge is not reloaded or discarded. This can also occur if the apparatus is inadvertently reloaded with a spent cartridge. Under such circumstances the fastening apparatus will fail to suture the body tissue, which can cause harm to the patient and result in the surgeon's loss of valuable time. The risk of harm is greatly increased if the apparatus contains a knife mechanism, since it will create an unsealed incision. To eliminate these dangers to the patient it would be beneficial to provide a mechanism which alerts the user that a new cartridge is required. It would further be beneficial if such a mechanism can provide a lock to actually prevent the surgeon from trying to fire a cartridge that has already been fired and prevent reloading of a spent cartridge. This would save valuable time and reduce the risks to the patient. The present invention relates to such an apparatus.

SUMMARY OF THE INVENTION

An apparatus is provided for applying a plurality of surgical fasteners to body tissue. The fasteners can be metal staples having deformable legs or two-part fasteners fabricated from bioabsorbable polymer such as polyglycolide, polylactide, and glycolide/lactide copolymer. The apparatus includes means for holding a fastener carrying cartridge; means for moving the fastener carry cartridge between a proximal first position and a distal second position wherein the cartridge is in close approximation to fastener closing means; means for substantially simultaneously ejecting the fasteners from the cartridge for closure thereof by the fastener closing means; approximation blocking means; and a locking member movable in response to the ejection of the fasteners and movement of the cartridge from the second cartridge position to the first cartridge position whereby the locking member becomes engageable with the approximation blocking means and prevents movement of the cartridge from the first cartridge position to the second cartridge position. The locking member is associated with the cartridge and is at least partially located inside the cartridge.

In one embodiment the approximation blocking means comprises a member having first and second slots, and the locking member includes a slot engaging rod which is movable between a first position wherein it is slidable into the first slot of the approximation blocking means and a second position wherein it is slidable into the second slot of the approximation blocking means.

In another embodiment the approximation blocking means comprises a surface for blocking distal movement of the locking member and the locking member is a drop bolt slidably mounted within the cartridge and movable from a first position to a second position wherein it is engageable with said approximation blocking means. Means is provided for biasing the locking member to the second position, and restraining means is provided for preventing the locking member from moving to the second position. The restraining means is movable from an initial restraining position to a non-restraining position when the fasteners are ejected from the cartridge.

BRIEF DESCRIPTION OF THE DRAWINGS

The invention is described in more detail hereinbelow wherein.

DETAILED DESCRIPTION OF THE INVENTION

Figure 1:
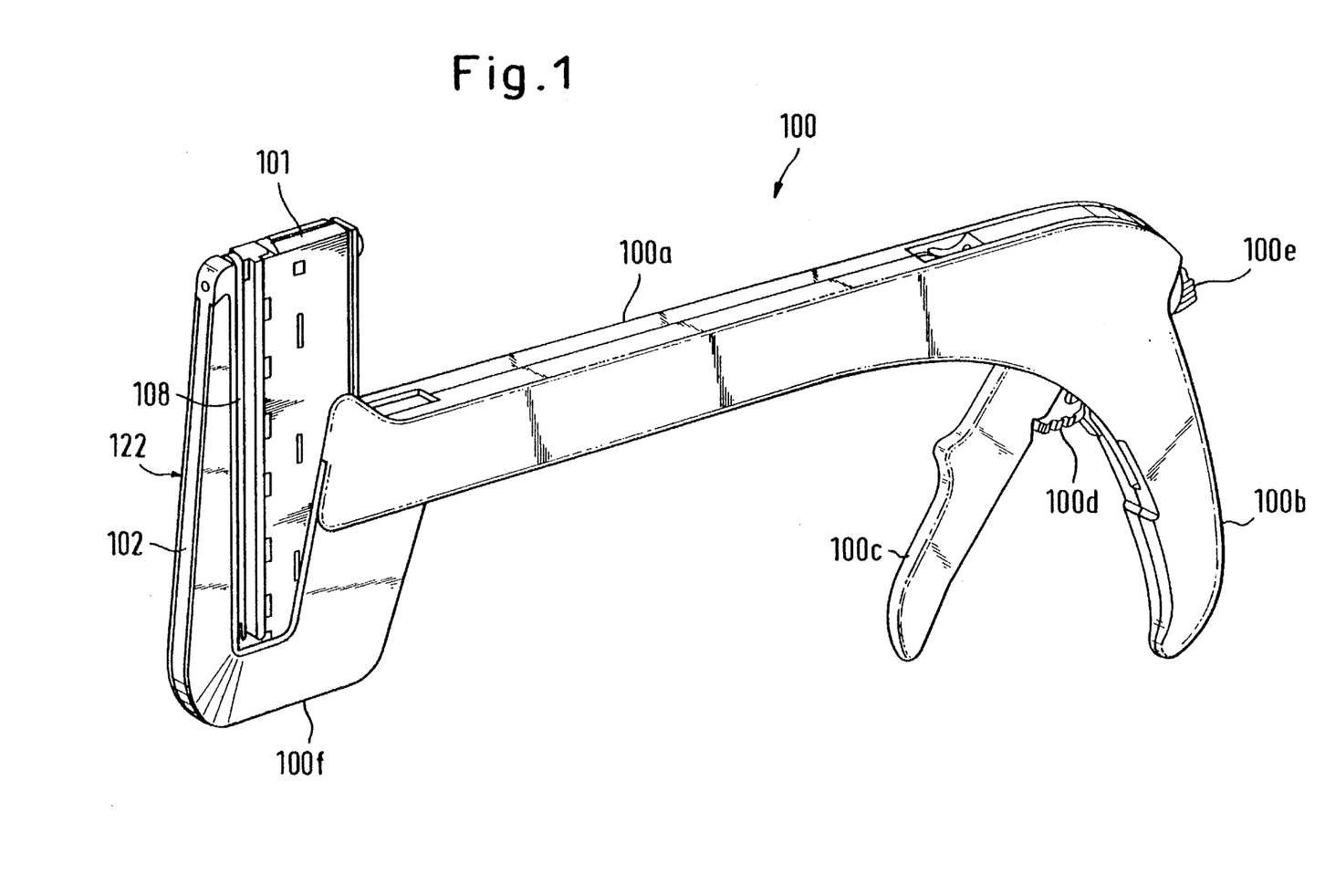
FIG. 1 illustrates a fastener applying apparatus in elevated perspective view.

FIG. 1 illustrates a surgical stapler 100 having an elongated carrier portion 100a, a handle 100b, an actuating lever or trigger 100c, a safety latch 100d for locking the trigger 100c, an approximating lever 100e, a U-shaped distal portion 100f, a staple holder cartridge 101, and an anvil assembly 122 comprising an anvil 108 for closing or crimping the staples and an anvil support arm 102. The instrument operates by positioning body tissue between the staple holder cartridge 101 and the anvil 108, then, by pivoting the approximating lever 100e, pivoting and sliding the staple cartridge 101 into a closed position wherein it is in close approximation to the anvil 108 so that it can grip tissue held therebetween. Next, the apparatus is fired by pressing the trigger 100c towards handle 100b, thereby substantially simultaneously driving surgical staples into the body tissue, the staple legs being crimped by anvil 108. Finally, the apparatus is opened by pivoting the approximation lever 100e to withdraw the cartridge 101 proximally away from the anvil assembly, thereby releasing the body tissue.

The term "fasteners" is used herein as a generic term which includes surgical staples, and the staple-shaped portion of two-part surgical fasteners, and equivalents thereof. Thus, although the surgical fastener of the present invention is exemplified in FIGS. 1–3 as a staple embodiment, the inventive features described herein are applicable to instruments for applying metal staples, as well as staples and two-part fasteners made from non-bioabsorbable or from bioabsorbable polymers (e.g. polyglycolide, polylactide and copolymers thereof). A two-part fastener is illustrated in FIG. 4. Unlike one piece staples which are closed by crimping the legs, the two piece fasteners are typically closed by joining and interlocking the two parts of the fasteners together. Typically, a two-part fastener includes a fastener portion 151 and a retainer portion 152. The fastener portion has prongs 153 which are adapted to be received into apertures 154 in the retainer and locked therein. The term "anvil assembly" is used herein as a generic term to include the anvil used to clinch surgical staples, the retainer holder and retainer member of two-part resinous surgical fasteners, and the equivalent of these elements. The anvil assembly of a fastener applying instrument holds the retainer portions until the fasteners are locked therein, whereupon the retainers are released.

Thus, the present invention should not be construed as being limited only to instruments for applying metal staples, but rather more generally to surgical fastener applying apparatus.

The locking mechanism of the present invention enables the apparatus to be fired only once in a single use, as it prevents reclosing of the apparatus, i.e., re-approximation of cartridge 101 after the fasteners have been fired and the cartridge 101 is retracted to its open position. If the cartridge 101 is adapted to be disposable and replaceable the apparatus can be refired by substituting a new cartridge loaded with staples. If reloaded with a spent (already fired) cartridge, the locking mechanism will prevent approximation of the cartridge and thereby not allow the instrument to be fired.

In general, the apparatus of the present invention includes a locking mechanism associated with the cartridge and an interference means, i.e. an approximation blocking means, associated with the anvil assembly. The approximation blocking means cooperates with the locking mechanism to prevent closure of the apparatus, that is, the cartridge 101 cannot be moved into close approximation with the anvil 108. In the illustrated embodiment (FIG. 2A), the approximation blocking means comprises a slot 104 formed in the anvil support arm 102 to provide a blocking surface at approximately a right angle to the motion of the cartridge. Alternately, one or more slots at differing angles could be provided to receive the locking mechanism. Clearly, the number, position, and configuration of the slots will vary depending on the locking mechanism employed. For example, if the locking mechanism is designed to extend linearly, the slot will extend longitudinally. Moreover, other blocking means besides slots can be provided as long as they achieve the function of engaging the locking mechanism to restrict movement of the cartridge.

As noted above, the locking mechanism of the present invention is associated with the cartridge and cooperatively engages the approximation blocking means so as to prevent distal movement of the cartridge beyond a predetermined position. The lockout mechanism is actuated after two movements have been completed: 1) firing of the fasteners from the cartridge, and 2) reopening the apparatus i.e. proximal movement of the cartridge to permit removal of tissue.

Figure 2A:
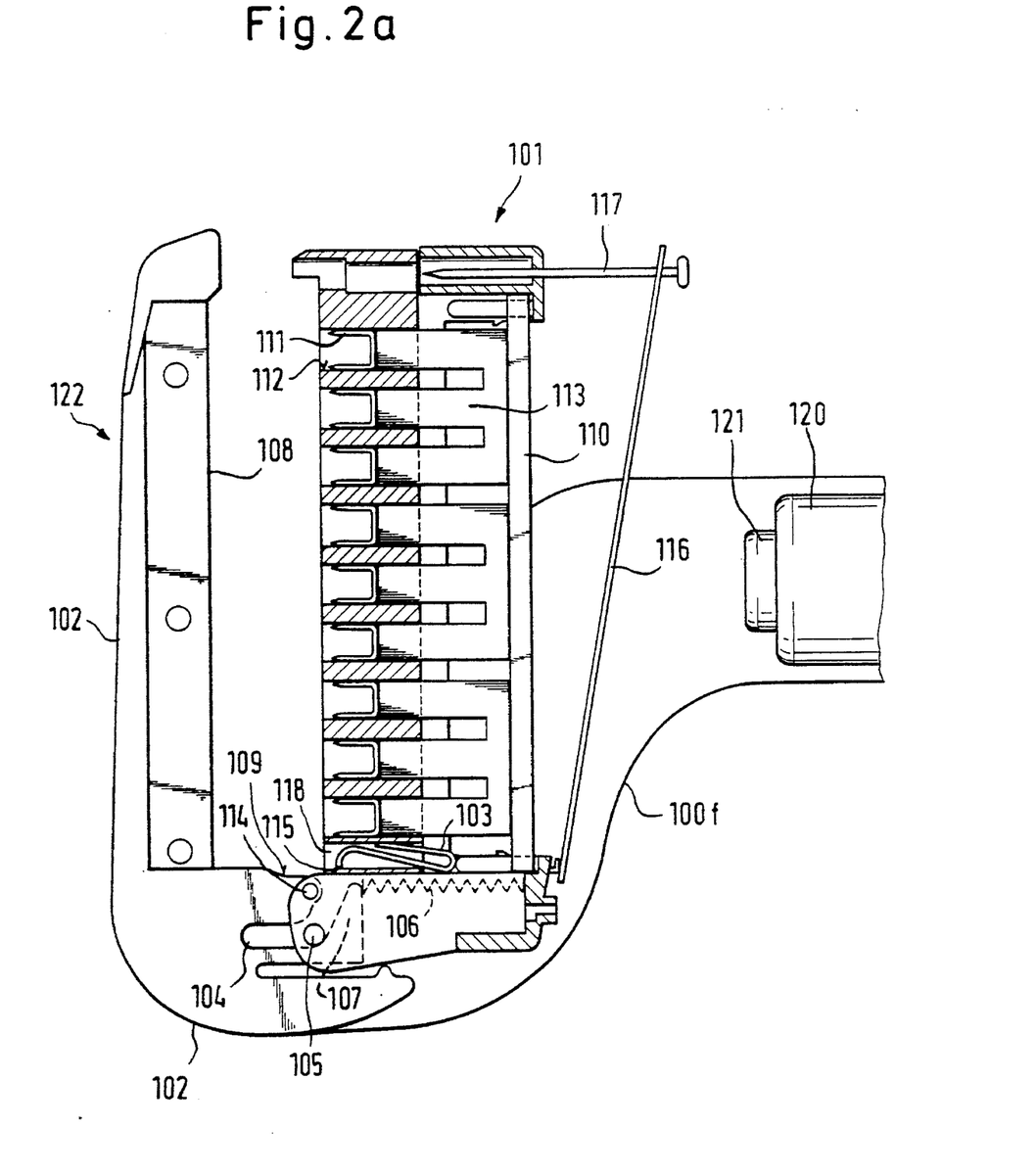
FIGS. 2a, 2b and 2c, illustrate in elevational sectional view the distal portion of the fastener applying apparatus in the pre-firing, fired, and after firing positions, respectively.
Figure 2B:
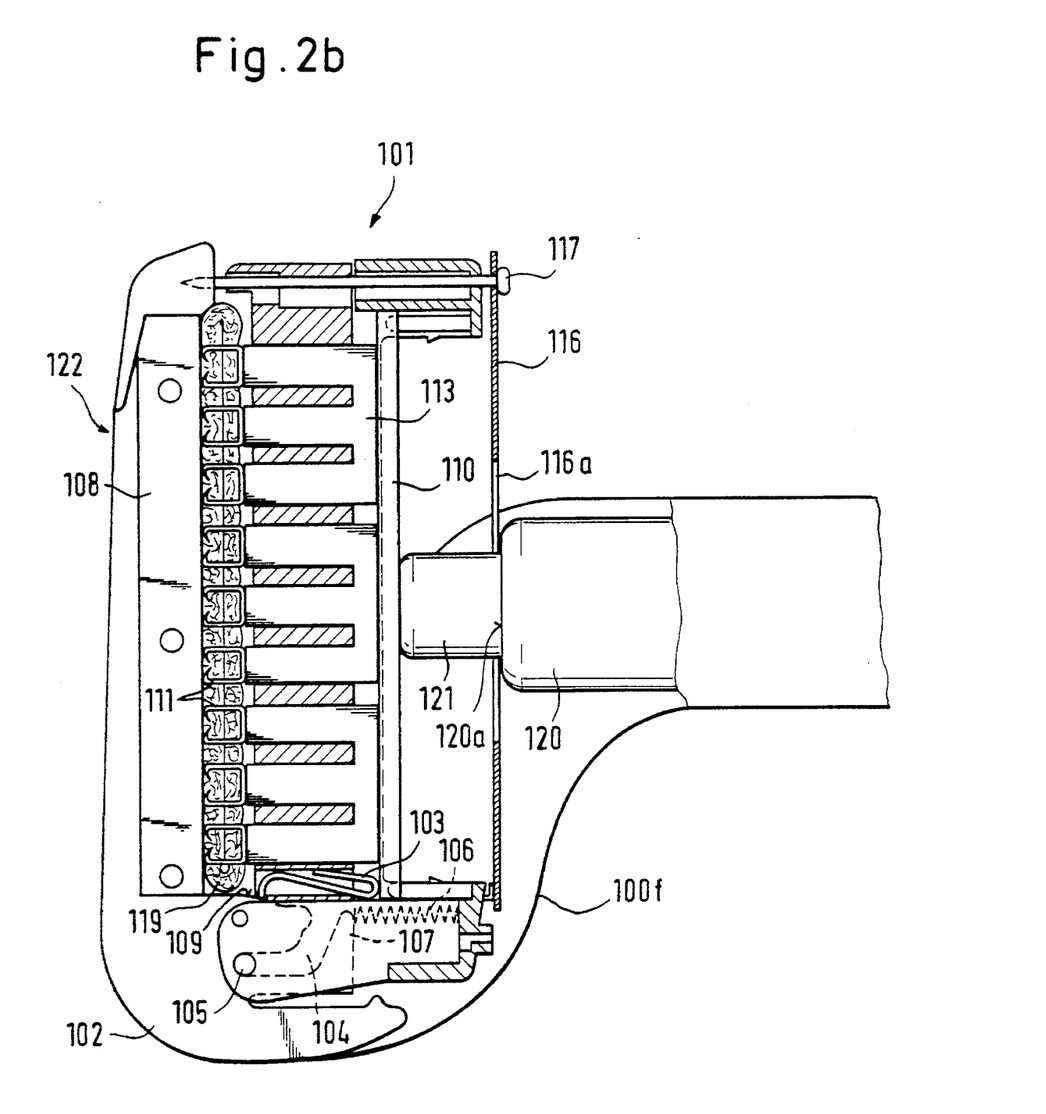
Figure 2C:
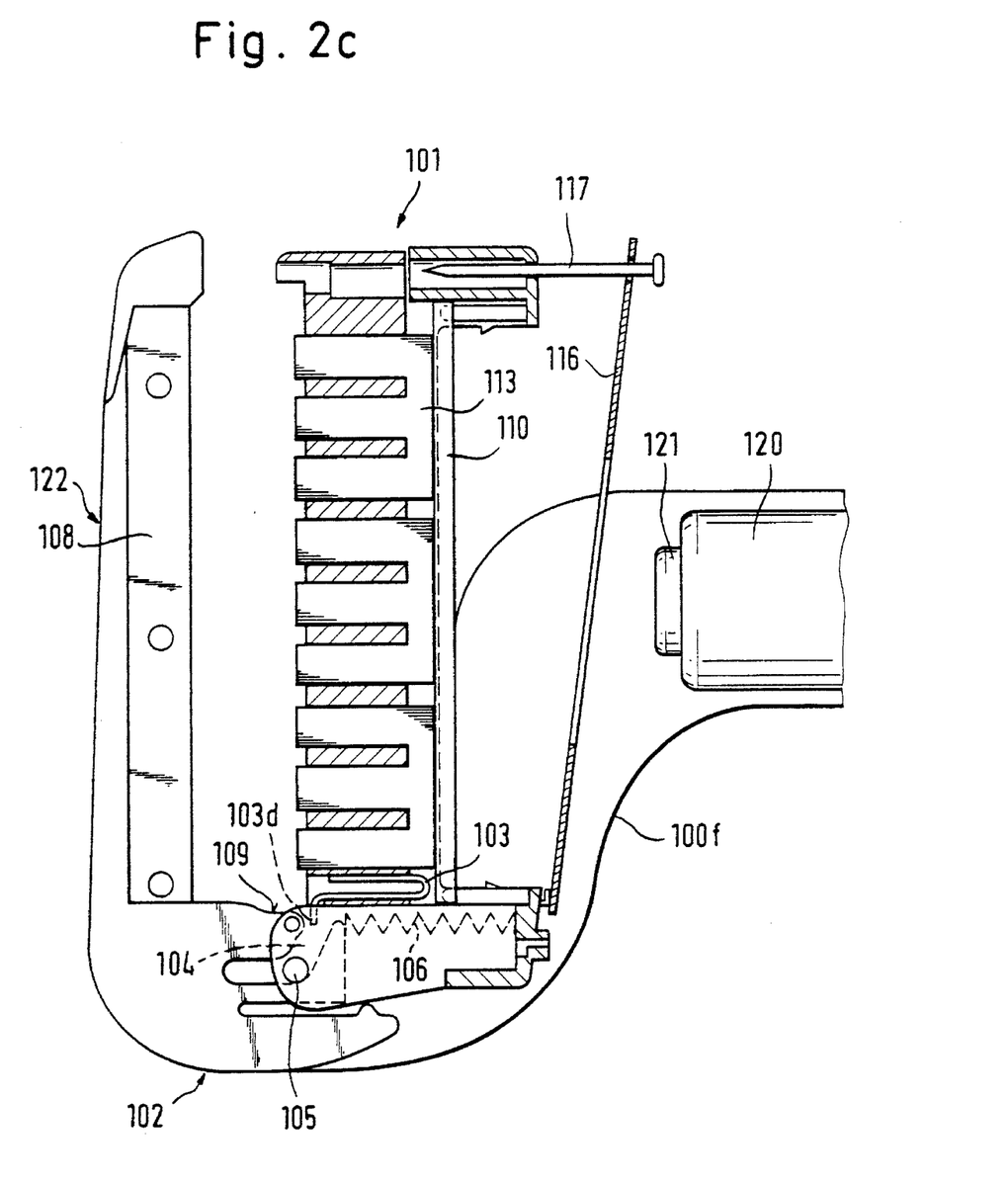
Figure 3A:
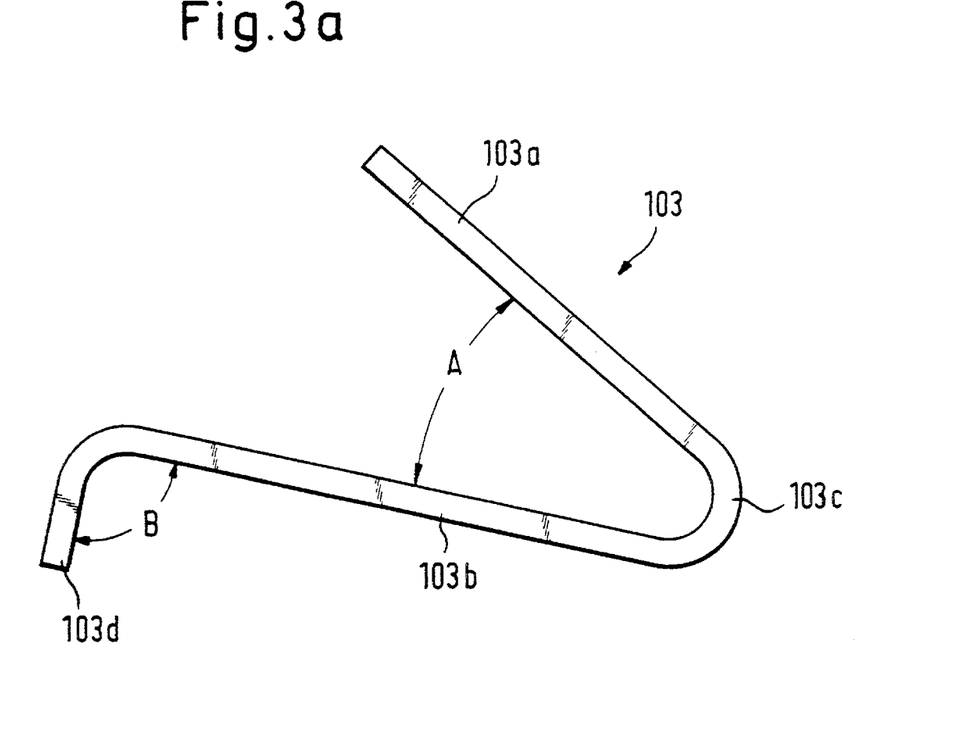
FIG. 3a illustrates a side view of the resilient locking clip.
Figure 3B:
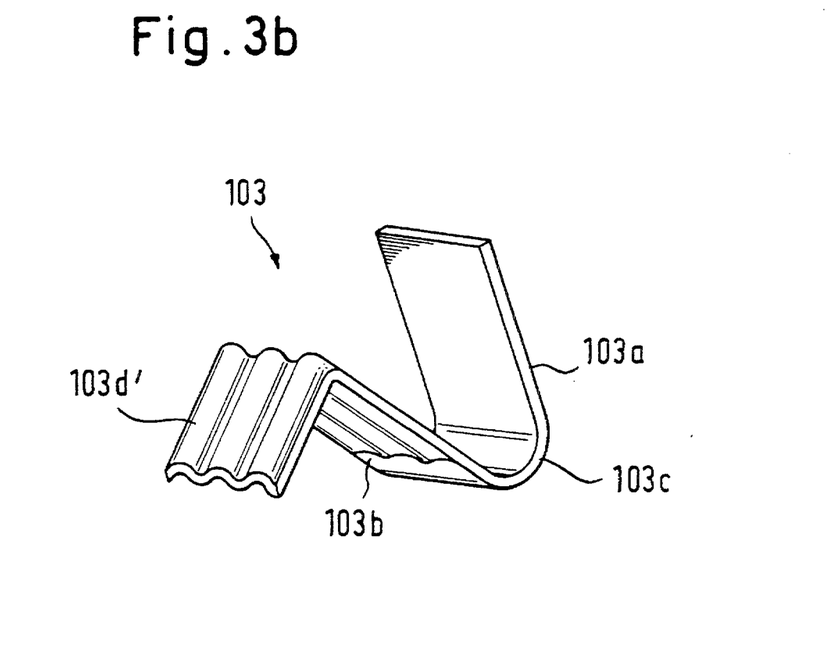
FIG. 3b is a perspective view of an alternative locking clip with ribbed hook portion.
Figure 4:
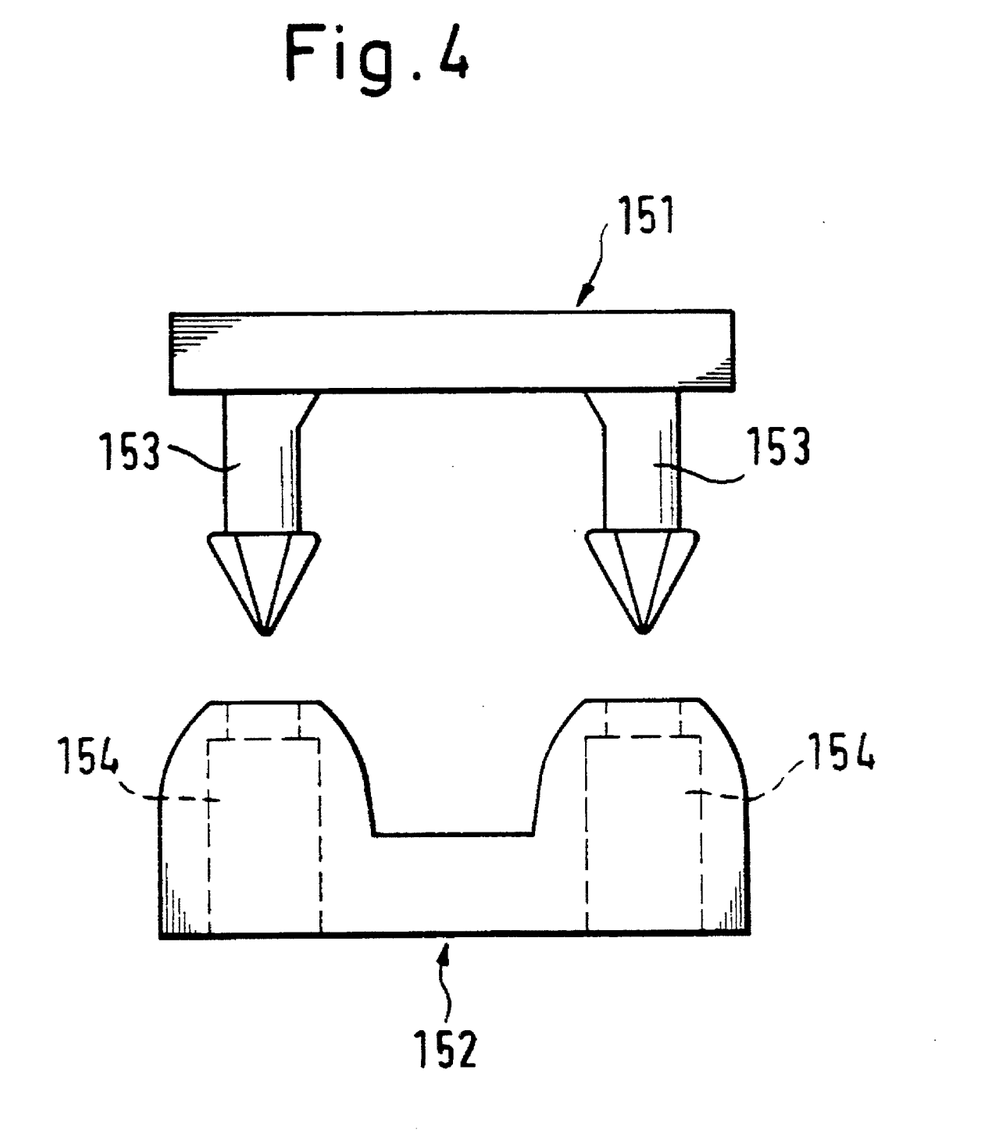
FIG. 4 is a side elevational view of a two-part surgical fastener.

In the embodiment shown in FIGS. 2 and 3, approximation blocking means is in the form of slot 104. The locking mechanism in this embodiment is designated by reference numeral 103 and includes a detent or hook 103d for engaging the slot. Cooperation between the locking mechanism and the walls of the slot 104 prevents movement of the cartridge 101 from the open (proximal) to the closed (distal) position. The hook 103d is moved out of its pre-fired position and into engagement with the slot 104 in response to actuation of the fastener driver which fires the fastener. The locking mechanism 103 is associated with the cartridge 101 so that removal and replacement of the cartridge effects a change of lockout mechanisms as well.

More specifically, the single use locking mechanism 103 in the embodiment of FIGS. 2 and 3 comprises locking clip 103 which is slidably mounted within chamber 118 of the cartridge 101. Referring additionally now to FIGS. 3a and 3b, locking clip 103 is preferably in the form of a leaf spring having a first, upper arm portion 103a and a second, lower arm portion 103b which are integrally united at curved proximal end 103c, and a hook 103d projecting downwardly from the distal end of the lower arm 103b. The upper arm 103a and lower arm 103b define an angle "A" which is about 10° to 50° depending on material thickness and condition, and preferably about 30°. The lower arm 103b and the hook 103d define an angle "B" which is preferably from about 75° to 120°. This area may be ribbed to provide additional resistance to bending when actuated. FIG. 3b illustrates a locking clip 103 with ribbed hook 103d'. The ribs may optionally also extend along lower arm 103b. The upper arm 103a is braced against the roof of the chamber 118, thereby providing a biasing force to resiliently urge lower arm 103b in a downward direction. The lower arm 103b illustratively extends longitudinally beyond that of upper arm 103a so that when the locking clip is moved distally as discussed below, the distal end of lower arm 103b with detent 103d is pushed outside chamber 118 while the upper arm 103a is still maintained inside the chamber 118 for providing the downward biasing force. In the initial position of locking clip 103, the hook 103d rests on base 115, which is preferably a strip of metal defining the floor of chamber 118. In this position the hook 103d is non-engageable with slot 104.

The hook can be integrally connected into a single piece to the locking clip in, for example, a resilient clip or a leaf spring with a hooked end. Alternately, the hook can be a separate piece connected to the locking clip.

FIG. 2a illustrates the distal portion of the apparatus 100 including the locking mechanism. In this embodiment the hook and locking member are integral. Fastener holder 101 is typically a rectangular shaped replaceable cartridge which is pivotally and slidably mounted to the anvil support arm 102 via mounting pin 105. The mounting pin 105, which is fixed to the lower portion of the staple cartridge 101, is adapted to be received into mounting slot 104 of the anvil support arm 102. Staples 111 are disposed within slotted grooves 112, and are pushed distally towards the anvil assembly by staple drivers 113 when the instrument is fired. The anvil assembly 122 comprises the anvil support arm 102 and, seated in the anvil support arm 102, an anvil 108 for crimping the legs of staples 111. Alignment pin 117, which is mounted to leaf spring 116, serves to align the cartridge 101 when the cartridge 101 is closed onto the body tissue. Spring 106 biases the cartridge 101 proximally, i.e., away from anvil assembly 122. The distal end of spring 106 abuts the proximal end of post 107, which is an integral part of anvil support arm 102.

Projections 114 project outwardly from the cartridge 101, and are adapted to abut the edge of U-shaped distal portion 100f when the apparatus is closed. Projections 114 serve to align the cartridge 101.

Further illustrations of fastener cartridges may be found in U.S. Pat. Nos. 4,568,009 and 4,915,100, herein incorporated by reference.

FIG. 2b illustrates the cartridge 101 in the fired position. Actuator 120 is moved distally when release toggle 100e is rotated clockwise, and the camming surface 120a is biased into contact with leaf spring 116. This moves the cartridge distally to close the apparatus on body tissue 119 located between the cartridge 101 and the anvil 108. Upon moving distally, spring 106 is compressed which then exerts a force for proximally biasing the cartridge back into the open position when the release toggle 100e is opened. When the actuating lever 100c is rotated counterclockwise, driver 121 is moved distally into contact with the pusher bar 110, moving the pusher bar 110 distally. The pusher bar, in turn, moves staple drivers 113 distally, thereby driving staples 111 through body tissue 119 and into the anvil 108 where the staple legs are crimped.

Upon moving distally, the pusher bar 110 also pushes locking clip 103 distally such that the hook 103d is moved out of chamber 118 and onto the sloped contact surface 109 of the anvil support arm 102. In this intermediate position, the hook does not yet engage the approximation blocking means.

After the stapling is completed, the apparatus is opened by rotating the approximating lever 100e counterclockwise back into the open position. As can be seen in FIG. 2c, after firing and release of approximation lever 100e, the cartridge 101 is moved proximally back into the open position to release the body tissue which was operated upon. However, the locking clip 103 does not fully return into chamber 118. Rather, the hook 103d slides down surface 109 and into the mouth of slot 104. The hook is held in this position by spring tension to prevent dislodging. Slot 104 in the anvil assembly thereby provides a catch means for engaging hook 103d. Once engaged therein, the locking clip prevents the apparatus from being reclosed, for if the user once again attempts to rotate lever 100e, the distal hook 103d will abut the edge of sloping surface 109 thereby preventing the cartridge 101 from being moved distally by actuator 120. At this time, either the expended cartridge can be removed, discarded, and replaced with a new cartridge, or the entire instrument can be discarded for a new instrument. The locking clip also prevents a fired or spent cartridge which has been removed and reinserted, from being closed since a spent cartridge when loaded will have its hook 103d seated in slot 104. An unfired cartridge on the other hand will have its hook 103d resting on the base 115 of the chamber 118 and therefore out of engagement with the slot in the anvil arm when inserted into the apparatus.

In an alternate embodiment of the locking mechanism shown in FIGS. 5–10, the locking mechanism is a T-shaped member pivotally mounted within the cartridge and removably held in sideways (longitudinal) position such that the trunk portion of the T is distally oriented. After firing of the fasteners, the T-shaped member is released. When the apparatus is opened, the T-shaped lockout member pivots downward and into alignment with a slot in an approximation blocking means associated with the U-shaped distal portion of the apparatus. If the user attempts to reclose the apparatus, i.e., move the cartridge distally by rotating lever 100e the trunk portion of the T-shaped locking mechanism will abut the distal wall of the slot and prevent further distal movement of the cartridge.

Figure 5:
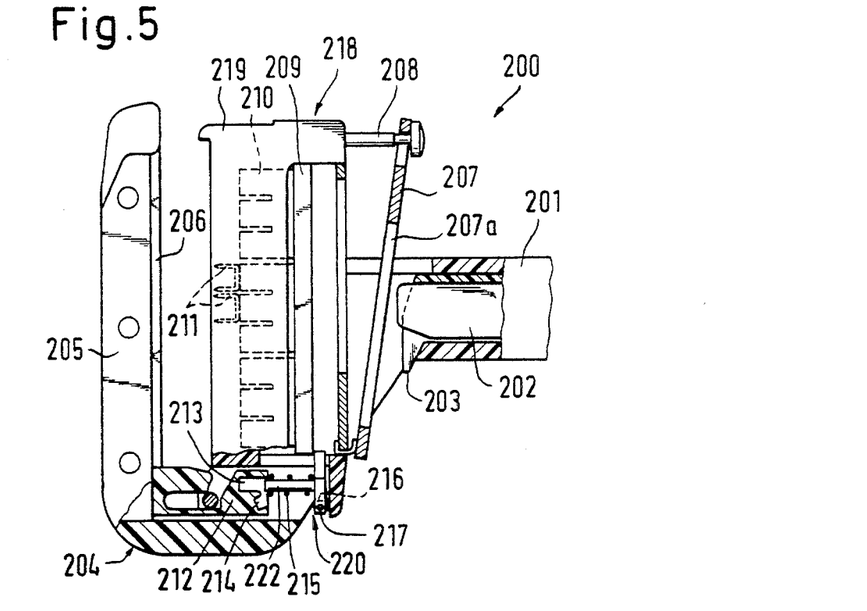
FIGS. 5 to 8 illustrate partially cut away side elevational views of an alternative embodiment of the locking mechanism of the present invention in four stages of operation, respectively: apparatus preclosed condition, apparatus closed but unfired, apparatus fired, apparatus reopened with attempted reclosure with spent cartridge.

Referring now more particularly to FIG. 5, the fastener applying apparatus 200 includes an elongated carrier 201 extending longitudinally and a U-shaped portion 204 at the distal end of the elongated carrier 201. The elongated carrier 201 includes driver 202 and actuator 203 extending longitudinally therein. The U-shaped distal portion 204 includes an anvil support arm 205 and anvil 206 mounted thereto. A cartridge 218 is mounted in the U-shaped distal portion 204 and is movable between an initial proximal position and a distal position wherein it comes into close proximity to anvil 206 for gripping body tissue therebetween. The cartridge 218 may be removable and replaceable, and includes body portion 219, a leaf spring 207, alignment pin 208, pusher bar 209, and staple driver 210. The fasteners, illustrated in FIG. 5 as staples 211, are located within slots in the cartridge 218 and are pushed by respective staple drivers 210 when the instrument 200 is fired such that the legs of staples 211 penetrate body tissue and are crimped by anvil 206. The U-shaped distal portion includes a stopping means, i.e., member 212, which includes an upper longitudinally oriented, preferably cylindrical, slot 213, and a lower slot 214 oriented at an angle from the longitudinal orientation of the apparatus 200, and of lesser depth than the upper slot 213. Clearly the slots can be formed of other shapes as long as they are configured and dimensioned to receive the locking mechanism.

Figure 9:
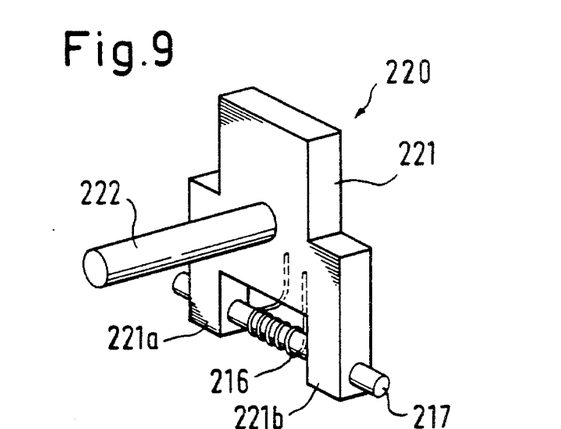
FIG. 9 illustrates the T-shaped locking member embodiment of FIGS. 5–8 of the present invention in perspective view.
Figure 10:
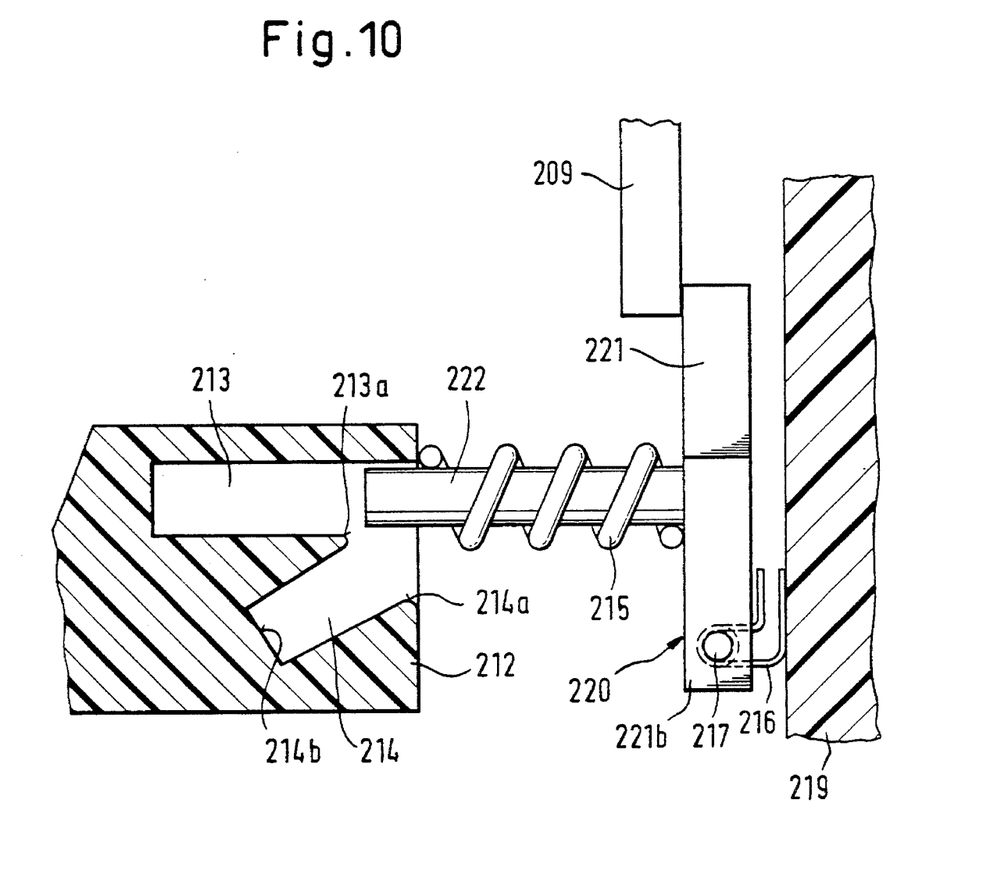
FIG. 10 illustrates a detailed partially sectional side elevational view of the T-shaped locking member and the approximation blocking means.

Referring now to FIGS. 5, 9, and 10, the T-shaped locking member 220 is pivotally mounted in cartridge 218. In the initial position, the back portion 221 of the locking member 220 is held upright by pusher bar 209. The back portion 221 includes depending legs 221a and 221b which are rotatably mounted to laterally extending shaft 217. Shaft 222 projects distally and perpendicularly from back 221. In the initial position of the locking member 220, shaft 222 is longitudinally oriented, and the distal end of shaft 222 projects a short distance into a reception area of the stopping means 212 where upper and lower slots 213 and 214 are joined.

Helical compression spring 215 applies a force for biasing the locking member 220 proximally. Preferably, spring 215 is of such length so as to apply biasing force when the locking member 220 is moved distally, but to apply little or no biasing force when the locking member 220 is in the initial or proximal position. Torsion spring 216 is coiled around shaft 217 and urges the locking member to pivot to a downward pointing position. In its downward pointing position, the distal end of the shaft 222 rests on the bottom edge 214a (FIG. 10) of the lower slot 214. The operational sequence of movements of the locking member 220 is explained more fully below.

In the initial prefired and open position, the apparatus 200 is in the condition as shown in FIG. 5. The cartridge 218 is in a proximal position, and, within the cartridge, the locking member 220 is held upright by the pusher bar 209, which is proximally located.

Figure 6:
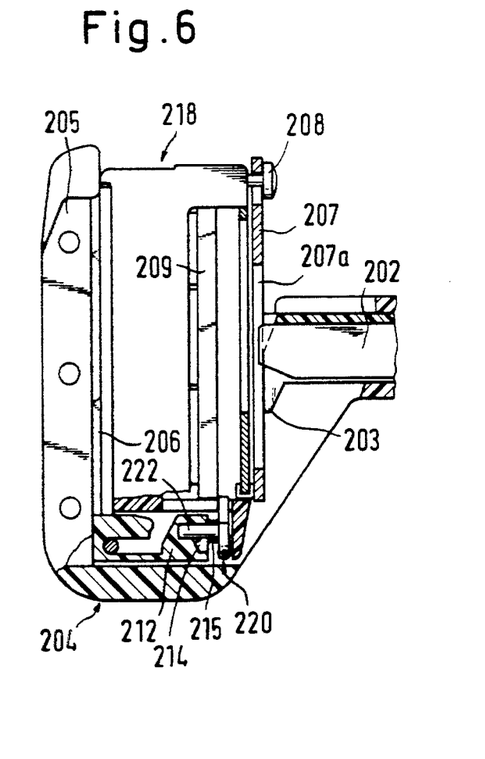

Referring to FIG. 6, when the apparatus is closed onto body tissue, i.e., when the cartridge 218 is approximated, actuator 203 is moved distally thereby moving cartridge 218 distally into close approximation with the anvil 206 so as to clamp body tissue therebetween. As can be seen in FIG. 6, the locking member 220 is moved distally against the biasing force of compression spring 215 such that shaft 222 is received into upper slot 213.

Figure 7:
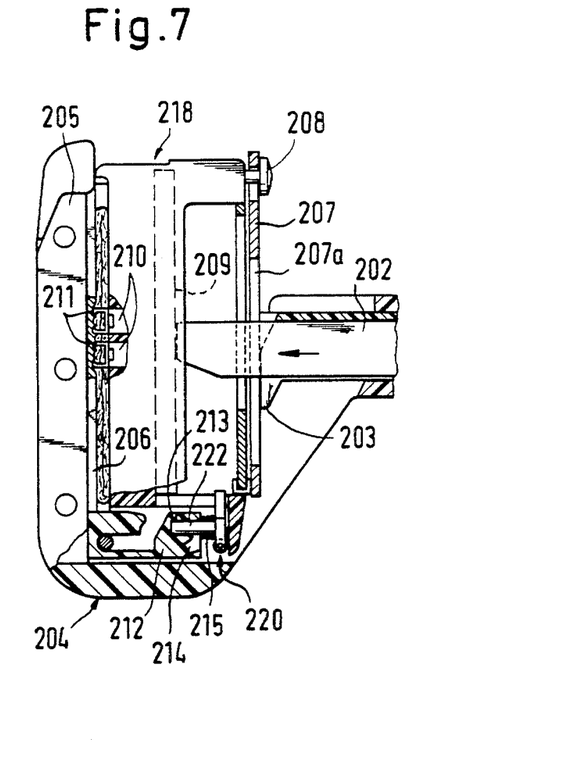
Figure 8:
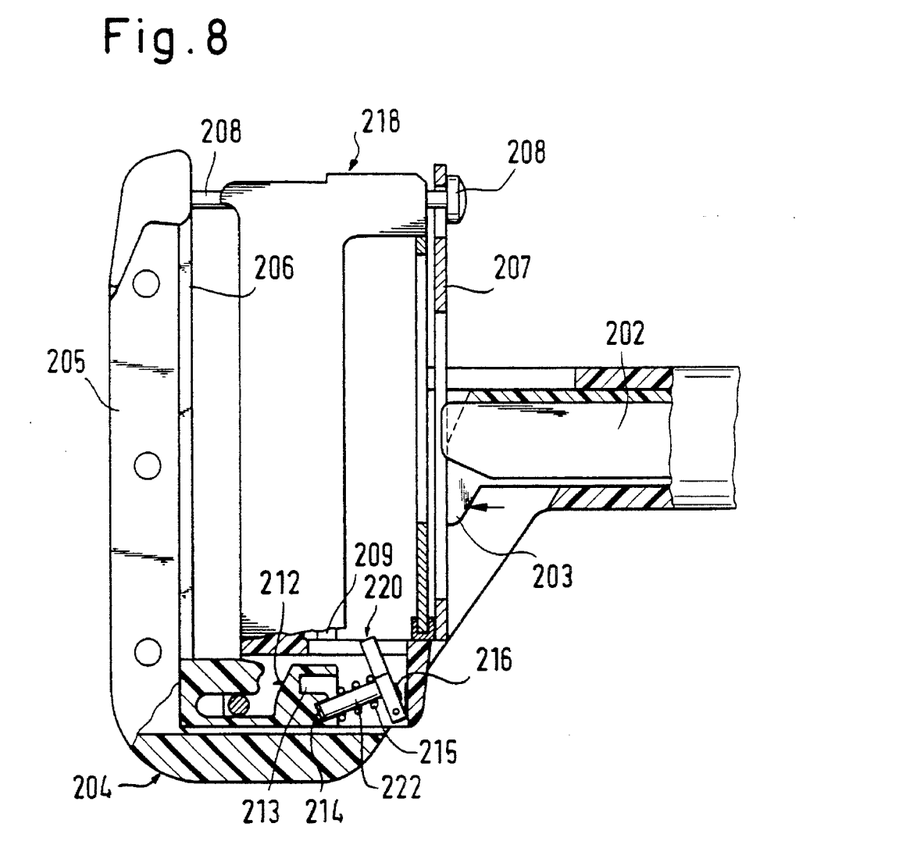

Referring now to FIG. 7., when the instrument is fired, driver 202 moves distally through slot 207a in the leaf spring and drives pusher bar 209 forward. Staple drivers 210 are, in turn, advanced so that staples 211 are substantially simultaneously driven through body tissue 230 and into the anvil 206 where they are crimped. The pusher bar 209 which had previously been restraining locking member 220 from pivoting downward, is moved to a position where it no longer provides such restraint and remains in the distal position even after the apparatus is reopened.

When the apparatus 200 is opened, i.e., the cartridge 218 is retracted to its proximal position and the actuator 203 is drawn back, the cartridge 218 is moved by the biasing force of compression spring 215 back to its proximal location. The distal end of the shaft 222 of locking mechanism 220 slides back out of the upper slot 213. Since there is no pivoting restraint, when the distal end of the shaft 222 rides over the bottom edge 213a of the upper slot (see FIG. 10), it drops down to the bottom edge 214a of the lower slot 214 under the biasing force of torsion spring 216.

Once the apparatus has been both fired and reopened, it cannot be reclosed, which is to say that the cartridge 218 cannot be reapproximated if it is spent. If an attempt is made to reapproximate the spent cartridge, the distal end of the shaft 222 will ride into the lower slot 214, which is not as deep as upper slot 213 and which cannot accommodate the full length of the shaft 222 (see FIG. 8). As shown in FIG. 10, slot 214 has a backstop surface 214b which prevents further distal movement of the locking member 220 or the cartridge 218. Thus, unless the spent cartridge 218 is replaced with a new cartridge, the instrument cannot be reclosed.

In another embodiment illustrated in FIGS. 11–16b, the locking mechanism may comprise a slidable shaft or drop bolt which is released upon firing of the apparatus, and which slides downwardly into a slot when the apparatus is opened (i.e. the cartridge is moved proximally) so that a portion of it protrudes beyond the lower surface of the cartridge thereby interfering with distal movement of the cartridge if an attempt is made to reclose the apparatus.

Figure 11:
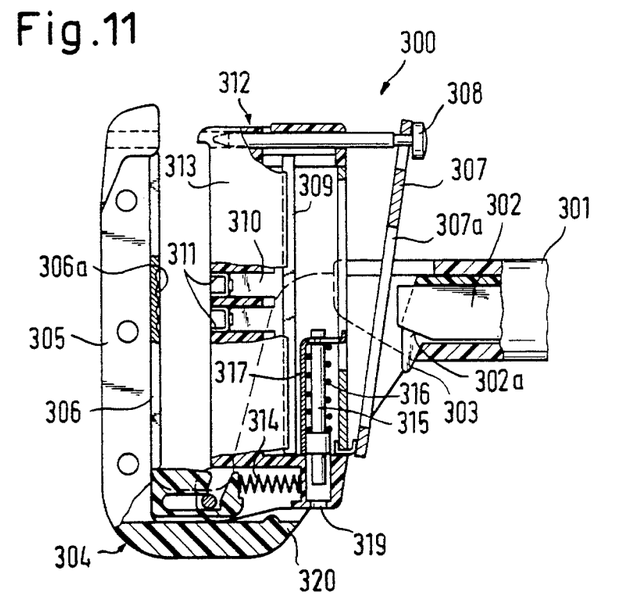
FIGS. 11 to 14 illustrate partially cut away side elevational views of another embodiment of the present locking mechanism of the present invention in four stages of operation, respectively: apparatus preclosed condition, apparatus closed but unfired, apparatus fired, and apparatus reopened with attempted reclosure with spent cartridge.

Referring now to FIG. 11, the fastener applying apparatus 300 includes an elongated carrier 301 extending longitudinally and U-shaped portion 304 at the distal end of the elongated carrier 301. The elongated carrier 301 includes driver 302 and actuator 303 extending longitudinally therein. The U-shaped distal end portion 304 includes an anvil support arm 305 and anvil 306 mounted thereto. A cartridge 312 is mounted in the U-shaped distal portion 304 and is movable between an initial proximal position and a distal position wherein it comes into close proximity to anvil 306 for gripping body tissue therebetween. The cartridge 312 may be removable and replaceable, and includes body portion 313, a leaf spring 307, alignment pin 308, pusher bar 309, and staple drivers 310. The fastener, illustrated in FIGS. 11, 12, and 13 as staples 311, are located within slots in the cartridge 312 and are pushed by staple drivers 310 when the apparatus 300 is fired, such that the legs of staples 311 penetrate body tissue and are crimped by in corresponding depressions 306a in anvil 306.

Figure 15:
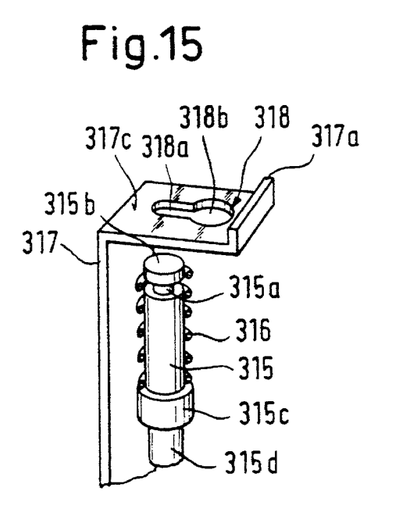
FIG. 15 illustrates the drop bolt embodiment of the locking mechanism of FIGS. 11–14 in perspective view.

Referring to both FIGS. 11 and 15, the cartridge 313 includes a drop bolt 315 maintained in an initial upper position as shown in FIG. 11, by a movable drop bolt retaining leaf spring 317. The leaf spring 317 includes an overhang portion 317c having a keyhole-shaped aperture 318 having a smaller and larger diameter portions 318a and 318b, respectively. The drop bolt 315 is mounted to the leaf spring retainer 317 such that the circumferential groove 315a of the drop bolt is disposed in the smaller diameter portion 318a of the aperture 318. The top portion 315b of the drop bolt 315 has a diameter smaller than that of aperture 318b so that it may pass through when the leaf spring is moved.

Helical compression spring 316 is disposed around drop bolt 315 such that the lower end of the spring 316 abuts the upper surface of collar 315c of the drop bolt. The upper end of spring 316 abuts the bottom surface of the overhang 317C, thereby applying a biasing force to urge the drop bolt to move downward. The drop bolt has a lower portion 315d which is receivable through aperture 319 (FIG. 11) in the cartridge so as to provide a stop means for engaging edge 320 of the U-shaped distal portion 304. The operational sequence of the locking mechanism of this embodiment is explained more fully below.

In the initial prefired and open position, the apparatus 300 is in the condition as shown in FIG. 11. The cartridge 312 is in a proximal position, and, within the cartridge, the drop bolt 315 is held in the upward position by leaf spring 317.

Figure 12:
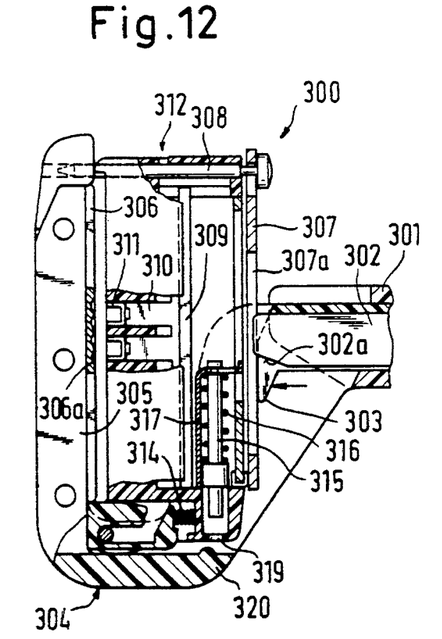

Referring to FIG. 12, when the apparatus 300 is closed onto body tissue, i.e., when cartridge 312 is approximated, actuator 303 is moved distally, moving cartridge 312 distally into close approximation with the anvil 306 so as to clamp body tissue therebetween. As can be seen in FIG. 12, the cartridge 312 is moved distally against the biasing force of compression spring 314.

Figure 13:
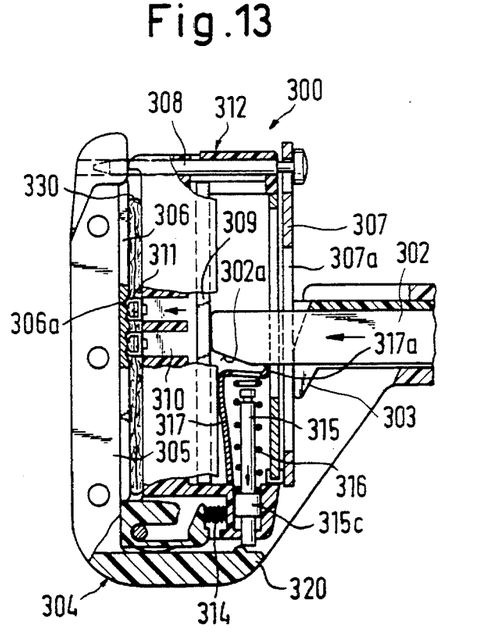

Referring now to FIG. 13, when the instrument 300 is fired, driver 302 moves distally through slot 307a in leaf spring 307, and moves pusher bar 309 forward. Staple drivers 310 are, in turn, advanced so that staples 311 are substantially simultaneously driven through body tissue 330 and into depressions 306a in the anvil 306 where the legs of staples 311 are crimped. The pusher bar 309, which had moved from its initial proximal position to the distal, or "fired" position, remains in the distal position even after the apparatus is opened.

Figure 16A:
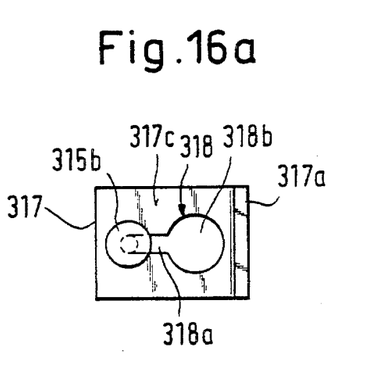
FIGS. 16a and 16b illustrate, in plan view, the drop bolt and the leaf spring bolt retainer in apparatus prefired, and apparatus fired condition, respectively.
Figure 16B:
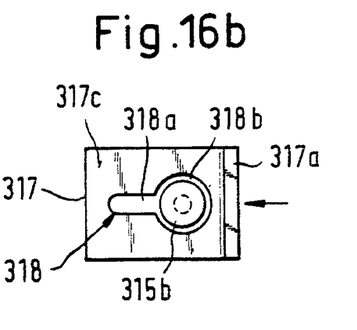

As can be seen from FIG. 13 and FIGS. 16a and 16b, when the staple driver 302 moves distally, the forward bottom edge 302a contacts proximal camming edge 317a of the drop bolt retaining leaf spring 317 and moves the top of the leaf spring 317 distally. When leaf spring 317 is moved distally, as shown in FIGS. 16a and 16b, the top portion 315b of the drop bolt 315 aligns with large diameter portion 318b of aperture 318, thereby permitting drop bolt 315 to disengage leaf spring 317 and to fall through. Spring 316 furthers this disengagement and, by providing biasing force on the drop bolt 315, insures that the drop bolt will disengage even if the apparatus is upside down with respect to gravity. Upon disengagement of the drop bolt 315 with the leaf retainer 317, the bottom portion 315d of the drop bolt drops through aperture 319 in the bottom of the cartridge and rests upon a shelf 304a of the U-shaped distal portion.

When the apparatus 300 is reopened, the actuator 303 is drawn back and the cartridge 312 is moved by the biasing force of compression spring 314 back to its proximal location. The bottom end of the drop bolt 315 slides over and down past edge 320. Collar 315c has a diameter larger than that of aperture 319 and, therefore, limits the distance which 315 drops.

Figure 14:
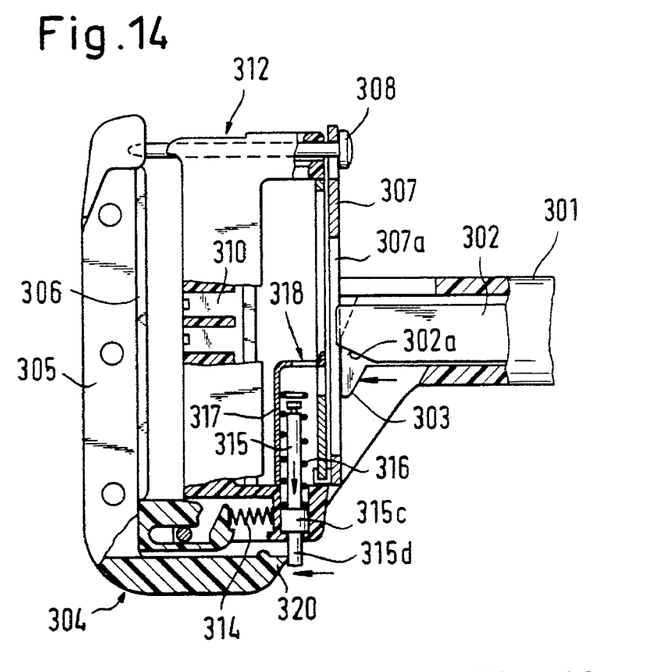

Once the apparatus 300 has been both fired and reopened, it cannot be reclosed which is to say that cartridge 312 cannot be reapproximated if it is spent. If an attempt is made to reapproximate the spent cartridge, as shown in FIG. 14, the bottom end 315d of drop bolt 313 will abut stop edge 320 and further distal movement of the cartridge 312 is prevented.

As is apparent from the above description, the locking mechanisms of the present invention can be utilized in stapling apparatus designed for single use, i.e., non-replaceable cartridges, which will prevent refiring of the spent cartridge. The locking mechanisms can also be used in apparatus utilizing replaceable cartridges and will prevent refiring if the apparatus is reloaded with a spent cartridge.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical fastener applying apparatus which comprises:

a) a cartridge for holding a plurality of surgical fasteners;

b) means responsive to application of a fastener driving force for substantially simultaneously ejecting surgical fasteners from said cartridge;

c) approximation blocking means for blocking approximation of said cartridge from a proximal position to a distal position; and d) a locking member supported within said cartridge, said locking member mounted for movement in response to application of said fastener driving force into engagement with said approximation blocking means only after fastener driving force into engagement with said approximation blocking means only after said surgical fasteners have been ejected from said cartridge to prevent reapproximation of the cartridge, said locking member including a generally cylindrical shaft portion.

2. The apparatus of claim 1, wherein said approximation blocking means comprises a member having first and second slots defined therein, and said locking member includes a slot engaging rod mounted for movement between a first position for sliding into said first slot of said approximation blocking means and a second position for sliding into said second slot of said approximation blocking means.

3. The apparatus of claim 2, wherein said second slot includes a wall surface for blocking distal movement of said slot engaging rod.

4. The apparatus of claim 2, wherein said locking member is pivotally mounted within the cartridge.

5. The apparatus of claim 2, further comprising means for biasing said locking member to said second position, and restraining means for preventing said locking member from moving to said second position, said restraining means being movable to a non-restraining position.

6. The apparatus of claim 5, wherein said means for biasing the locking member to said second position comprises a torsion spring.

7. The apparatus of claim 5, wherein said restraining means comprises a pusher bar one end of which contacts and blocks the locking member, said pusher bar being movable responsive to a fastener driving force applied thereto to move to a non-restraining position.

8. The apparatus of claim 5, wherein said means for biasing said locking member to said second position comprises a helical compression spring.

9. The apparatus of claim 8, wherein said helical compression spring is disposed around said locking member.

10. The apparatus of claim 1, wherein said cartridge is removable and replaceable.

11. The apparatus of claim 1, wherein said approximation blocking means comprises a surface for blocking distal movement of the locking member.

12. The apparatus of claim 1, wherein said fasteners comprise metal staples.

13. The apparatus of claim 1, wherein said fasteners comprise two-part fasteners fabricated from bioabsorbable polymer, said two-part fasteners comprising a fastener portion and a retainer portion.

14. The apparatus of claim 13, wherein said bioabsorbable polymer is selected from the group consisting of polyglycolide, polylactide, and glycolide/lactide copolymer.

15. The apparatus of claim 1, wherein said generally cylindrical shaft portion is movable from a first position to a second position wherein it is engageable with a blocking surface associated with said approximation blocking means.

16. The apparatus of claim 15, wherein said cartridge includes means for biasing said locking member to said second position, and restraining means for preventing said locking member from moving to said second position.

17. The apparatus of claim 16, wherein said restraining means is movable from an initial position to a non-restraining position.

18. The apparatus of claim 17, wherein said restraining means comprises a resilient member having means to releasably engage one of two end portions of said locking member, said resilient member being movable to said non-restraining position in response to application of a fastener driving force.

19. The apparatus of claim 18, wherein said locking member comprises a cylindrical shaft having a circumferential groove at said one end portion.

20. The apparatus of claim 19, wherein said means to releasably engage said one end portion of the locking member comprises an aperture in said resilient member having a relatively narrow portion and a relatively wide portion, said narrow portion having a width less than the diameter of said locking member but of sufficient width to engage the locking member at said groove, and said wide portion of the aperture having a greater size than the diameter of the locking member so as to allow said locking member to pass therethrough.

21. The apparatus of claim 20, wherein the cartridge includes an aperture for permitting passage of the other of the two end portions of the locking member to a position wherein it is engageable with the approximation blocking means.

22. The apparatus of claim 16, wherein said restraining means comprises a pusher bar, one end of which contacts and blocks said locking member, said pusher bar being movable in response to fastener driving force applied thereto to move said pusher bar to a non-restraining position.

23. The apparatus of claim 22, wherein said restraining means further comprises a resilient member having means to releasably engage one of two end portions of said locking member, said resilient member being movable to said non-restraining position in response to application of fastener driving force.

24. The apparatus of claim 16, wherein said locking member is pivotally mounted within said cartridge and said means for biasing said locking member to said second position comprises a torsion spring.

25. The apparatus of claim 16, wherein said locking member is slidably mounted within said cartridge and said means for biasing said locking member to said second position comprises a helical compression spring.

26. The apparatus of claim 1, wherein at least a portion of said locking member extends beyond the periphery of said cartridge for engaging said approximation blocking means when said locking member is moved into said second position.

27. A surgical stapler comprising:

an anvil frame elongate in a longitudinal direction and including anvil surfaces in a plane generally perpendicular to the longitudinal direction;

a cartridge assembly movable relative to the anvil frame between an open position with the cartridge assembly spaced from the anvil surfaces and a closed position with the cartridge assembly and the anvil surfaces in closely spaced relationship, said cartridge assembly including a cartridge housing containing a plurality of staples disposed in at least one row positioned in opposition to the anvil surfaces, and a pusher plate for pressing the staples within the cartridge housing against the anvil surfaces to engage and close the staples in tissue between the cartridge housing and the anvil surfaces, said pusher plate being movable relative to the cartridge housing between pre-fired and fired positions; and means for preventing the cartridge assembly from moving from the open to the closed position when the stapler is loaded with a cartridge housing having a pusher plate in a fired position, said means for preventing said cartridge assembly from moving from said open to said closed positions including a first retention aperture and a second safety aperture opening into the surface of the anvil frame for engagement with a locking pin, said locking pin supported within said cartridge assembly and mounted for movement between a first position engaged with said first retention aperture to afford free movement of the cartridge assembly between the open and closed positions, and a second blocking position engaged with said second safety aperture to prevent movement of the cartridge assembly from said open to said closed position, and a biasing mechanism for urging the locking pin toward the blocking position.

28. A surgical stapler according to claim 27, wherein the biasing mechanism comprises a coil spring having a first end connected to the second end of the locking pin and a second end connected to the bottom surface of the safety aperture.

* * * * *